(12) United States Patent
Domke et al.

(10) Patent No.: US 9,683,972 B2
(45) Date of Patent: Jun. 20, 2017

(54) METHOD AND DEVICE FOR EXAMINING A SHEET-SHAPED OR CARD-SHAPED VALUABLE DOCUMENT HAVING A SECURITY FEATURE HAVING ONE OR MORE CAVITIES

(71) Applicant: GIESECKE & DEVRIENT GMBH, Munich (DE)

(72) Inventors: Jan Domke, Vaterstetten (DE); Stefan Kokrhoun, Grobenzell (DE); Patrick Renner, Reichersbeuern (DE); Andre Gregarek, Munich (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 395 days.

(21) Appl. No.: 14/354,635

(22) PCT Filed: Oct. 25, 2012

(86) PCT No.: PCT/EP2012/004475
§ 371 (c)(1),
(2) Date: Apr. 28, 2014

(87) PCT Pub. No.: WO2013/060465
PCT Pub. Date: May 2, 2013

(65) Prior Publication Data
US 2014/0290367 A1 Oct. 2, 2014

(30) Foreign Application Priority Data
Oct. 28, 2011 (DE) .................. 10 2011 117 239

(51) Int. Cl.
*G01N 29/36* (2006.01)
*G01N 29/11* (2006.01)
(Continued)

(52) U.S. Cl.
CPC .......... *G01N 29/36* (2013.01); *B42D 25/346* (2014.10); *G01N 29/04* (2013.01); *G01N 29/11* (2013.01);
(Continued)

(58) Field of Classification Search
None
See application file for complete search history.

(56) References Cited

U.S. PATENT DOCUMENTS 8,230,742 B2 7/2012 Domke et al.
8,333,870 B2 12/2012 Burchard et al.
(Continued)

FOREIGN PATENT DOCUMENTS

CN        1681668 A    10/2005
CN     101528474 A     9/2009
(Continued)

OTHER PUBLICATIONS

German Search Report from corresponding German Application No. 10 2011 117 239.8, issued Jun. 19, 2012.
(Continued)

*Primary Examiner* — Paul West
*Assistant Examiner* — Mark A Shabman
(74) *Attorney, Agent, or Firm* — Workman Nydegger

(57) ABSTRACT

A method is for examining a sheet-shaped or card-shaped value document with a security feature having one or more cavities configured in the value document. The width of the cavity or cavities is in at least one respectively specified direction exceeding 10 µm. Transmission values are established in a locally resolved manner for the transmission of ultrasound in a specified frequency range. In employing the transmission values, it is checked whether a specified number of transmission values is greater than a specified transmission threshold value.

20 Claims, 9 Drawing Sheets

(51) Int. Cl.
*G07D 7/08* (2006.01)
*G01N 29/34* (2006.01)
*G01N 29/04* (2006.01)
*B42D 25/346* (2014.01)

(52) U.S. Cl.
CPC .............. *G01N 29/348* (2013.01); *G07D 7/08* (2013.01); *B42D 2033/22* (2013.01); *B42D 2035/16* (2013.01); *B42D 2035/36* (2013.01); *G01N 2291/0237* (2013.01)

(56) References Cited

U.S. PATENT DOCUMENTS

| | | | |
|---|---|---|---|
| 8,510,062 B2 | 8/2013 | Domke et al. | |
| 8,534,708 B2 | 9/2013 | Heim et al. | |
| 2005/0206500 A1 | 9/2005 | Ferren et al. | |
| 2006/0127649 A1 | 6/2006 | Keller et al. | |
| 2009/0001709 A1 | 1/2009 | Kretschmar et al. | |
| 2009/0312957 A1* | 12/2009 | Domke | G01N 29/0618 702/39 |
| 2010/0061619 A1 | 3/2010 | Boegli | |
| 2010/0132470 A1 | 6/2010 | Domke et al. | |
| 2010/0194091 A1* | 8/2010 | Heim | B42D 25/29 283/85 |
| 2012/0266678 A1 | 10/2012 | Domke et al. | |

FOREIGN PATENT DOCUMENTS

| | | |
|---|---|---|
| DE | 102005045566 A1 | 9/2006 |
| DE | 102006033001 A1 | 1/2008 |
| DE | 102006061337 A1 | 6/2008 |
| EP | 1667073 A1 | 6/2006 |
| WO | 2008009384 A1 | 1/2008 |
| WO | 2008134910 A1 | 11/2008 |
| WO | 2009/021738 A1 | 2/2009 |

OTHER PUBLICATIONS

International Search Report from corresponding PCT Application No. PCT/EP2012/004475, Feb. 5, 2013.
International Preliminary Report on Patentability from corresponding PCT Application No. PCT/EP2012/004475, Apr. 29, 2014.

* cited by examiner

Fig. 9
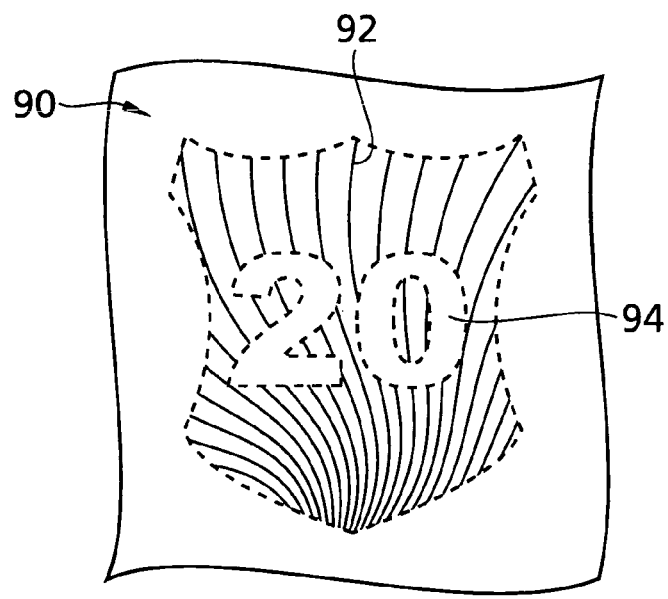
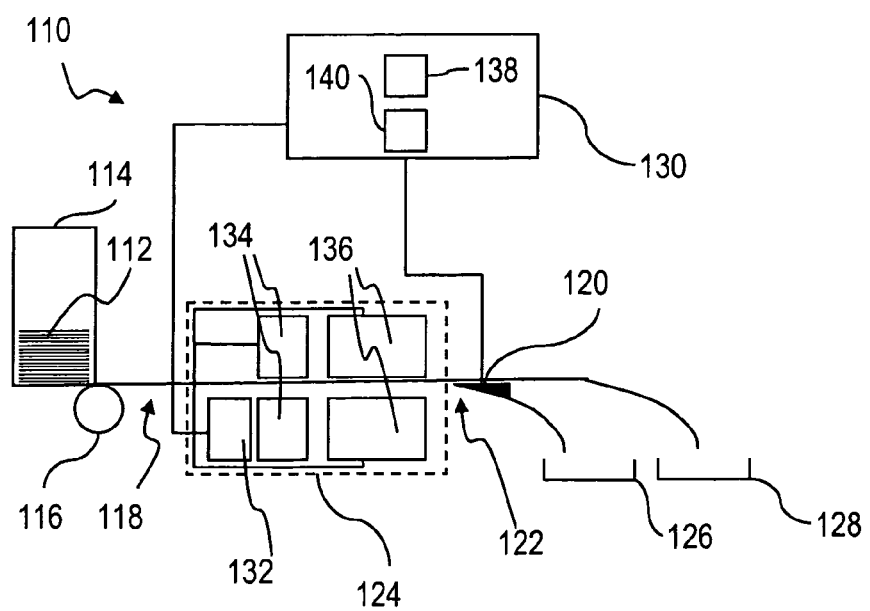
Fig. 10

METHOD AND DEVICE FOR EXAMINING A SHEET-SHAPED OR CARD-SHAPED VALUABLE DOCUMENT HAVING A SECURITY FEATURE HAVING ONE OR MORE CAVITIES

BACKGROUND

The present invention relates to a method for examining a sheet-shaped or card-shaped value document with a security feature having one or more cavities configured in the value document, and to a corresponding apparatus for carrying out the method.

SUMMARY

Value documents are understood here to be sheet-shaped or card-shaped objects that represent for example a monetary value or an authorization and hence should not be manufacturable arbitrarily by unauthorized persons. Such value documents have features that are not easily manufactured or copied, whose presence is an indication of authenticity, i.e. manufacture by an authorized body. Important examples of such value documents are chip cards, coupons, vouchers, checks and in particular bank notes.

The present invention is based on the object of impeding the making and/or use of forged value documents.

This object is achieved by a method according to claim 1 and in particular a method for examining a sheet-shaped or card-shaped value document of a specified type with a security feature having one or more cavities configured in the value document, the width of the cavity or cavities in at least one respectively specified direction exceeding 10 µm, wherein transmission values are established in a locally resolved manner for the transmission of ultrasound in a specified frequency range, and wherein, employing the transmission values, the criterion is checked of whether a specified number of transmission values is smaller than a specified transmission threshold value which corresponds to a transmission that is smaller than the transmission of at least one reference region of the value document or of at least one reference value document not having the cavity or cavities. In dependence on the result of the check a signal is then preferably formed which represents an indication of the authenticity of the value document and/or which represents an indication of the presence of a forgery of the value document. The signal can be so formed that it only represents an indication of the authenticity of the value document when the criterion is satisfied, and/or always represents an indication of the presence of a forgery when the criterion is not satisfied. The signal can in particular also be employed for storing a corresponding authenticity value in a memory of a data processing device employed in the check, said value representing corresponding indications and being employable subsequently.

The method according to the invention serves for examining a certain type of value documents, namely value documents with at least one security feature having one cavity or a plurality of cavities. When the security feature has a plurality of cavities, they can be of the same or different form and size. The cavity or cavities have an extension in at least one direction specified for the cavity or for the respective cavity of at least 10 µm. Cavities for the purposes of this invention are closed.

Preferably, the extension of the cavity or cavities in the or another direction specified for the respective cavity, parallel to a surface of the value document, amounts to more than 100 µm.

The extension of the cavity or cavities in a direction perpendicular to the surface of the value document is preferably greater than 30% of the total thickness of the value document in the region of the cavity or cavities and/or greater than 20 µm.

Preferably, the cavity or at least two of the cavities are of line-shaped configuration. The line-shaped cavities are preferably configured with a width between 0.05 mm and 1 mm. The center-to-center distance of nearest neighboring line-shaped cavities advantageously lies between 0.05 mm and 1 mm, in particular between 0.3 mm and 0.7 mm, whereby the center-to-center distance can be constant (equidistant cavities) or variable (divergent cavities).

To enable an especially good recognition of the security feature upon the examination with ultrasound, a surface representing an orthogonal projection of the cavity or cavities onto the surface of the value document has a proportion of the surface of the security feature of greater than 10%, preferably than 30%. The surface of the security feature is understood here to be the surface of the smallest region of the surface of the value document that is formed by at least one closed curve and in which the projection of the cavity or the projections of the cavities lie. This smallest surface is preferably greater than 5 mm$^2$.

The stated dimensions and shapes allow a good recognition of the security feature with ultrasound, on the one hand, and a simple manufacture, on the other hand.

The cavity or cavities can in principle be manufactured in any way. Preferably, the value document comprises a substrate which has for the cavity or each of the cavities a partial or, particularly preferably, complete piercing which is covered on both sides by cover layers held on the substrate, so that the covered piercing forms the cavity. This enables an especially simple manufacture of the security feature or value document. For example, the substrate can comprise at least one layer of bank-note paper/or a polymeric foil, and the cover layers can comprise a polymeric foil or a polymeric film. Alternatively, the substrate can be formed for example from at least one polymeric material or plastic, and the cover layers can be made of paper. The bank-note paper or paper can be made of natural fibers and/or synthetic fibers or contain natural fibers and/or synthetic fibers.

The piercings can be disposed in a motif region of the value document, which preferably has a changed visual impression in incident light and/or transmitted light and/or is configured in the form of a pattern, signs or an encoding. A changed visual impression in incident light and/or transmitted light is understood here to mean that the visual impression is changed upon viewing in incident light compared to viewing in transmitted light. This enables a simple visual check of the security feature with the naked eye.

Particularly preferably, the piercings can be of line-shaped configuration and preferably have a width between 0.05 mm and 1 mm. This enables in particular a simple manufacture of the cavities.

In a preferred embodiment, the motif region has partial piercings, i.e. depressions, and these partial piercings are formed by a multiplicity of thinning lines in the substrate. These then result in line-shaped cavities. In the region of the partial piercings the motif region then shows a watermark-like appearance wherein the represented motif is hardly recognizable in incident light, i.e. in reflected light, while it appears clearly in transmitted light due to the higher light transmission of the partly pierced regions.

At a layer thickness SD of the substrate, the partial piercings can have a depth Ti according to the following relation: 0<Ti<SD. That is, the depth Ti of the partial piercings can reach a value that is only slightly smaller than the layer thickness SD of the substrate.

When the piercings are not tactilely detectable, the security feature can be only machine-testable, depending on the optical design. Preferably, the piercings are tactilely detectable, however. To ensure the tactility of the motif region, the partial piercings have a depth of approx. 10 μm or more. It will be appreciated that the tactility of the material depends not only on the depth T of the (partial) piercings, but e.g. also on the width B of the (partial) piercings. It has turned out in practice that the tactility of the motif region is ensured at a depth of approx. 10 μm or more and a width of approx. 100 μm or more.

Alternatively or additionally, the motif region can have complete piercings, and these complete piercings are particularly preferably formed by a multiplicity of cut lines in the substrate. In the region of the complete piercings the motif region then constitutes a transmission-view region in the value document, which is recognizable both upon plan viewing and in transmission view. Piercings formed by cut lines form in particular line-shaped cavities. The motif region preferably has a surface area of at least 4 mm². This allows reliable detection with ultrasound in the preferred frequency range.

In all designs, the cut lines or thinning lines are preferably configured with a width between 0.05 mm and 1 mm. The center-to-center distance advantageously lies between 0.05 mm and 1 mm, in particular between 0.3 mm and 0.7 mm, whereby the center-to-center distance can be constant (equidistant cut lines or thinning lines) or variable (divergent cut lines or thinning lines).

The substrate of the value document can be formed by a plastic foil, in particular an opaque plastic foil of PET, PP, PE, PA, PC (polycarbonate) or PVC. If the substrate is not opaque in accordance with the definition given hereinbelow, it can advantageously have a transmittance smaller than 10% or even be configured so as to be non-transparent. The layer thickness of the (opaque) plastic foil typically lies between 4 μm and 100 μm, and in particular at about 50 μm. It will be appreciated that the layer thickness of the substrate is chosen in particular in dependence on the nature of the foil material employed and of the layer construction of the polymer bank note.

The polymeric cover layers are advantageously configured so as to be transparent or translucent. To retain the tactility of the motif region to the greatest possible extent, the polymeric cover layers are configured very thin, preferably with a thickness of 12 μm or less, and in particular with a thickness of about 6 μm or less. For example, a polymeric cover layer can have a thickness of only approx. 4.5 μm, thereby retaining the tactility of the motif region very well.

A polymeric cover layer is preferably formed by a plastic foil, in particular of PET, PP, PE, PA, PC or PVC, a plastic foil of PET being particularly preferable at present.

On at least one of the polymeric cover layers there is advantageously provided an ink-receiving layer disposed in some regions or over the full surface, which serves the further design of the value document by printing technology. The ink-receiving layer is advantageously of opaque configuration. There can be associated with such an opaque ink-receiving layer a third optical transmittance, while there can be associated with the substrate a first optical transmittance, and with the region of the piercings in the substrate a second optical transmittance which is greater than the first optical transmittance. If the third optical transmittance is smaller than the second optical transmittance, there results upon viewing of the motif region of the value document a changed visual impression in incident light and/or transmitted light.

For the purposes of the present patent application, optical transmittance designates the transmissivity to light, in particular to light in the visible wavelength region between 400 nm and 800 nm, i.e. to light as is usually perceived by the viewer. Depending on the application, however, optical transmittance can also refer only to a single wavelength or to other wavelength regions, for example to the near UV or IR wavelength region adjoining the visible spectral region. A non-transparent layer ideally has an optical transmittance of 0%, this value normally not being exactly reached in practice. A transparent layer ideally has an optical transmittance of 100%, this value normally not being exactly reached in practice.

Within the framework of the present patent application, a translucent layer preferably has an optical transmittance such that a viewer can unmistakably distinguish a translucent layer from a non-transparent and a transparent layer. Accordingly, a translucent layer has an optical transmittance that differs sufficiently clearly from the optical transmittances of a non-transparent and a transparent layer. Within the framework of the present patent application, a translucent layer hence preferably has an optical transmittance of 10% to 90%, and particularly preferably of 20% to 80%. When the optical transmittance refers not only to a single wavelength but to a wavelength region, for example the visible spectral region, optical transmittance describes the optical transmittance of the different wavelengths lying within the wavelength region, averaged over the respective wavelength region. Preferably, the optical transmittance in a wavelength region assumes the same value for each wavelength of the wavelength region. The optical transmittance of a layer describes the ratio of passed light to incident light upon passage through the layer, for example in the normal direction of the layer.

An opaque layer, in particular an opaque ink-receiving layer for the purposes of the present application is a layer that, upon viewing in incident light, at least substantially, but ideally completely hides structures lying behind the layer in the viewing direction, for example further layers, so that these structures lying further back are no longer perceived by a viewer. In other words, the term "opaque" relates primarily to a viewing in incident light, with this optical property again relating to the relevant wavelength or relevant wavelength region. The relevant wavelength region is typically the visible spectral region between 400 nm and 800 nm, but can alternatively or additionally also relate to the bordering wavelength regions in the near UV region or IR region.

Further, an opaque layer does not necessarily have to be non-transparent, but can have an optical transmittance greater than 0%. An opaque layer, in particular an opaque ink-receiving layer on at least one of the polymeric cover layers of the value document, has such properties. For this purpose, the material, the layer thickness and other properties of the opaque layer, in particular of the opaque ink-receiving layer, are chosen suitably. Therefore, the opaque ink-receiving layer is preferably a layer that enables the physical drying or the film formation of oil-based printing inks and/or of aqueous and/or organic-solvent-containing and/or cationically or radically curing printing inks. The opaque ink-receiving layer can be manufactured on an aqueous basis and/or on the basis of organic solvents. The opaque ink-receiving layer can further be present as a single layer or be constituted in the form of a plurality of single layers which can differ with respect to their material constitution. The total layer thickness of the opaque ink-receiving layer can preferably lie in a range of 2 μm to 15 μm. The opaque ink-receiving layer preferably contains self-cross-linking resins and/or at least two components to be cross-linked with each other. The first component can preferably be chosen among alkoxy silanes, isocyanates, diimides, aziridines and glycidic ethers. The second component can preferably be chosen among polyurethanes, urethane acrylates, polyesters, polyethers, polyvinyl alcohols, maleinates, acrylates and copolymers thereof. Further, the opaque layer can in particular contain fillers, such as silica gels, metal oxides, metal hydroxides; metal-oxide hydrates, salts of inorganic acids. At a sufficiently small layer thickness, the ink-receiving opaque layer appears milky or cloudy in transmitted light.

The value document can of course also have further layers, such as protective layers, or function layers provided with other security elements. Expediently, the polymeric cover layers are respectively connected to the substrate via a laminating-adhesive layer.

In an advantageous embodiment, the motif region has in its interior at least one region, without piercings of the substrate, which is configured in the form of a pattern, signs or an encoding.

Such a value document can be manufactured for example by making available a substrate made of bank-note paper and/or a polymeric material, forming in the substrate a motif region in which tactilely detectable, partial or complete piercings are made in the substrate in the form of a pattern, signs or an encoding, thereby producing the motif region with the changed visual impression in incident light and/or transmitted light, and respectively covering the substrate on both sides, at least in the motif region, by a cover layer, preferably a polymeric cover layer.

The piercings can be produced for example with a punch, but they are preferably produced by lasering, in particular by means of a CO2 laser, due to the higher spatial resolution.

The polymeric cover layers are advantageously laminated onto the substrate at least in the motif region, this preferably being done after the partial or complete piercings are produced.

In the method, for checking the security feature there is preferably employed ultrasound that has a frequency in the range of 50 kHz to 800 kHz. Further, it is preferred that ultrasonic pulses are employed for establishing the transmission values. In this case, the frequency of the ultrasound is understood to be the arithmetic average over the frequencies of the pulse.

Transmission values are understood within the framework of the present invention, when referring to ultrasound, to be transmission values for ultrasound in the specified frequency range, unless otherwise expressly described.

In particular, in the method, an extension of the cavity or cavities respectively in a specified direction parallel to a surface of the value document is preferably smaller than a wavelength of the ultrasound in air.

For establishing the ultrasound transmission values there can be employed a locally resolving ultrasound transmission sensor which is configured for employment in the specified frequency range. It can preferably have mutually opposing ultrasonic transmitters and ultrasonic receivers between which, for detecting the transmission values, the value document is transported through by means of a transport device, the transmission values being detected during the transport through. The ultrasonic paths respectively formed between the ultrasonic transmitters and ultrasonic receivers can be aligned so as to be inclined or preferably substantially orthogonal relative to a transport plane in which the value documents are transported through the ultrasound transmission sensor.

Upon the check, the transmission values are tested as to whether a specified number thereof undershoot the transmission threshold value. The transmission threshold value is chosen here so as to correspond to a transmission that in a specified manner is smaller than the transmission of at least one reference region having no cavity. The reference region which can be specified for the specified type of value document can be a reference region of the currently checked value document or of reference documents of the specified type. The transmission of a reference region is understood here to be the average transmission of the reference region, preferably an arithmetic average. The specified number is preferably chosen in dependence on the extension of the security feature or the value-document type and the local resolution of the ultrasonic sensor or the transmission measurement. Preferably, the number is greater than 1.

The check can be effected by means of an electronic circuit or preferably a data processing device, which can have for example an FPGA and/or a microcontroller and/or a processor. The check can be effected by direct comparison of the respective transmission value with the transmission threshold value, by comparison of a value of a function, which is monotonic, preferably strictly monotonic, in the relevant values range, of the transmission value for the respective transmission value with the one threshold value corresponding to the value of the function for the transmission threshold value, or in another indirect manner. In the second case, the transmission threshold value does not necessarily have to be specified itself, it may instead suffice to state the threshold value. The function does not have to be monotonically increasing, it can also be monotonically decreasing. In the latter case, it is then checked whether the function value for the respective transmission value is smaller than the threshold value.

The transmission threshold value can in principle be specified in any way. It does not necessarily have to correspond exactly to the stated transmission of the reference regions, but can also be chosen for example smaller, for example between 1 and 20% smaller.

Thus, the transmission threshold value can be established while employing the transmission values established for the checked value document. Preferably, such transmission values are established for the reference region of the value document where no cavities are to be expected.

As a transmission threshold value there can be employed for example an average, in particular arithmetic average, of such transmission values.

However, it is also possible for example that the first transmission reference value has been established by examinations of reference value documents of the same type. Reference value documents of the same type are understood in the case of bank notes to be authentic value documents of the same currency and denomination which have the security feature. This allows a particularly reliable establishment of a suitable transmission threshold value.

A particularly reliable check results when, in the method, it is established upon the check of the criterion whether the respective transmission value lies within an interval whose upper limit is the transmission threshold value. The lower limit is preferably chosen in dependence on transmission values that result upon detection of overlapping portions of two value documents of the specified type that are superimposed but not stuck together. Preferably, the lower limit is chosen so as not to be smaller than a double removal threshold value for the transmission values which is employed for recognizing, by means of the ultrasound transmission sensor, value documents of the specified type that are being transported in at least partly superimposed arrangement. Preferably, the limit lies at least 5% above the double removal threshold value.

In principle, in the method, the entire value document can be used for the check. However, it is also possible that, in the method, only transmission values for a specified region of the value document are employed in the check. The region can be specified in particular in dependence on the type of the value document. For example, it may be a region where cavities must be expected to be found in an authentic value document of the specified type.

In principle, it is sufficient, in the method, that only the presence of the specified number of transmission values is checked upon the check. However, it is also possible that, in the method, the distribution of the transmission values in the specified region and/or of those transmission values in the specified region that are smaller than the transmission threshold value is additionally taken into consideration upon the check. The check can then be classified as successful only when the distribution satisfies a specified distribution criterion. The criterion with regard to the number must then be additionally satisfied. In particular, the distribution criterion can be a criterion for the presence of a specified pattern of transmission properties or transmission values or detectable cavities.

Depending on the position and shape of the cavities, there can additionally be checked, in the method, the further criterion of whether the locations corresponding to the specified number of transmission values or of the transmission values undershooting the transmission threshold value form a contiguous structure. Preferably, the signal is then so formed that it represents an indication of the authenticity of the value document only when the further criterion is satisfied, or that it represents an indication of the presence of a forgery whenever the further criterion is not satisfied.

The subject matter of the invention is also an apparatus for examining a sheet-shaped or card-shaped value document with a security feature having one or more cavities configured in the value document, the width of the cavity or cavities in at least one respectively specified direction exceeding 10 μm, which has an ultrasound transmission sensor for detecting locally resolved transmission values for the transmission of ultrasound in a specified frequency range through the value document, and a control and evaluation device connected to the ultrasound transmission sensor via a signal connection, which is configured for carrying out the method according to the invention. Preferably, the apparatus further comprises a transport device for transporting the value document through the ultrasound transmission sensor, the apparatus being so configured that the transmission values are detected during the transport of the value document through the ultrasound transmission sensor. The control and evaluation device can in particular have a data processing device which has for example an FPGA and/or a microcontroller and/or a processor and a memory with a data processing program stored therein, which in particular carries out the check, as mentioned hereinabove.

BRIEF DESCRIPTION OF THE DRAWINGS

The invention will hereinafter be explained further by way of example with reference to the drawings. Therein are shown.

DETAILED DESCRIPTION OF VARIOUS EMBODIMENTS

Figure 1:
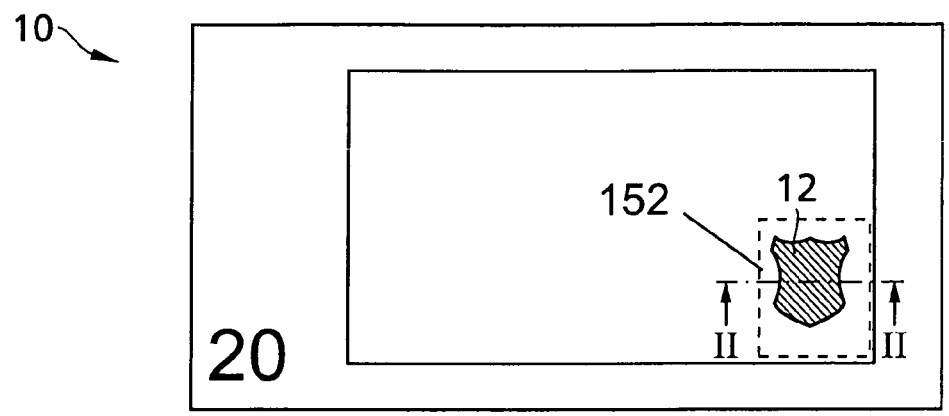
FIG. 1 a schematic representation of a polymer bank note having a motif region.
Figure 2:
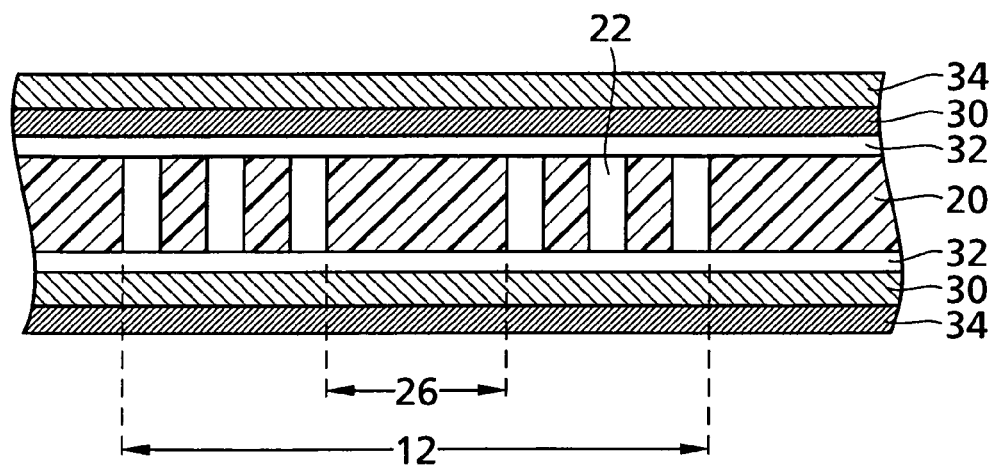
FIG. 2 a cross section through the polymer bank note of FIG. 1 along the line II-II, FIG. 3 a detail plan view of the transmission-view region of the bank note of FIG. 1, FIG. 4 for a polymer bank note according to another exemplary embodiment, a cross section only through the polymer substrate in the motif region, FIG. 5 the visual appearance of the motif region of the finished polymer bank note of FIG. 4, FIG. 6 for a polymer bank note according to a further exemplary embodiment of the invention, a cross section only through the polymer substrate in the motif region, FIG. 7 for a polymer bank note according to yet another exemplary embodiment, in (a) a cross section only of the polymer substrate, in (b) the visual impression of the motif region in plan view, and in (c) the visual impression of the motif region in transmission view, FIGS. 8 and 9 the visual appearance of the motif region of finished polymer bank notes according to further exemplary embodiments, FIG. 10 a schematic representation of a bank-note processing apparatus, FIG. 11 a schematic representation of an ultrasonic sensor of the bank-note processing apparatus in FIG. 10 with a control and evaluation device in a view along a transport direction of value documents, FIG. 12 a schematic representation of ultrasonic transmitters of the ultrasonic sensor in FIG. 11 in a plane parallel to the plane of a value document to be examined, FIG. 13 a schematic partial representation of a value document with spots or sensing regions acoustically irradiated by the ultrasonic transmitters of the ultrasonic sensor in FIG. 11, FIG. 14 a schematic representation of a value document with locations or sensing regions for which transmission values have been established by means of the ultrasonic sensor in FIG. 12, FIG. 15 a simplified flowchart of a method for examining a sheet-shaped or card-shaped value document by means of the ultrasonic sensor and the control and evaluation device in FIG. 11 according to a preferred embodiment of the invention, FIG. 16 a simplified flowchart of a method for examining a sheet-shaped or card-shaped value document by means of the ultrasonic sensor and the control and evaluation device in FIG. 11 according to a further preferred embodiment of the invention, and FIG. 17 a simplified flowchart of a method for examining a sheet-shaped or card-shaped value document by means of the ultrasonic sensor and the control and evaluation device in FIG. 11 according to a further preferred embodiment of the invention.

The invention will now be explained by the example of value documents in the form of polymer bank notes. FIGS. 1 and 2 thus show a schematic representation of a polymer bank note 10 which has a motif region in the form of a transmission-view region 12 according to the invention. The transmission-view region 12 of the polymer bank note 10 is shown more precisely in FIG. 2 in cross section along the line II-II, and in FIG. 3 in a detail plan view.

Figure 3:
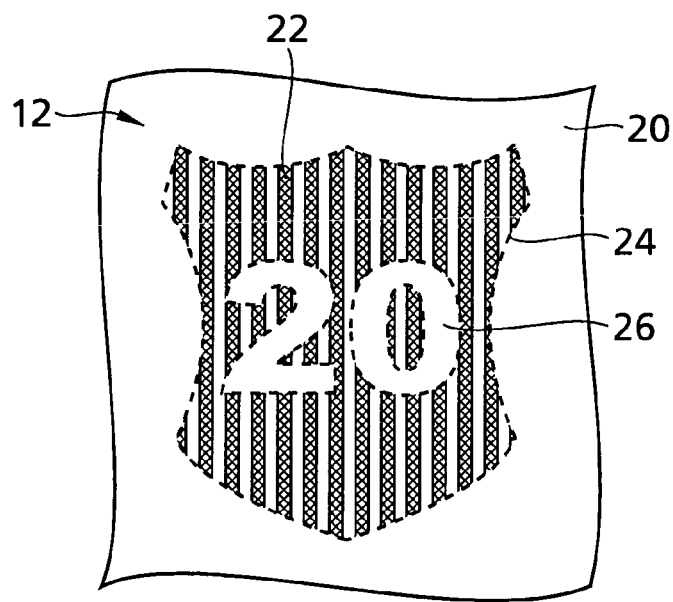

Referring to FIGS. 2 and 3, the bank note 10 has a substrate 20 in the form of an opaque or even non-transparent, 50-µm-thick PET foil. In the opaque or even non-transparent polymer substrate 20, exposure to the radiation of a $CO_2$ laser has made a line grid which is formed from a multiplicity of parallel, through-going cut lines 22. For the sake of better recognizability, the cut-out regions of the polymer substrate 20 are represented unfilled in the cross section of FIG. 2, while the cut-out lines 22 are shown by hatching in the plan view of FIG. 3.

The line grid of the cut lines 22 has in the shown exemplary embodiment a period length of 0.75 mm at a cutting width of the cut lines of 0.25 mm. The surface coverage of the line grid thus amounts to 33%, so that the transmission-view region 12 is recognizable upon viewing both in plan view and in transmission view.

As best recognized in FIG. 3, the cut lines 22 are so disposed that the line grid constitutes a motif in the form of a pattern, signs or an encoding. In the shown exemplary embodiment, the transmission-view region 12 constitutes with its outer outline 24 a coat of arms which contains in its interior an uncut region 26 in the form of the denomination "20" of the polymer bank note 10. The outlines of the coat of arms 24 and of the denomination 26 that are shown by dashed lines in the figure serve only to illustrate the constituted form in the drawing and do not necessarily correspond to a contour actually present on the bank note.

Returning to the representation of FIG. 2, the two opposing sides of the transmission-view region 12 have laminated thereon, by means of two laminating-adhesive layers 32, respectively an only 6-µm-thick, transparent, translucent, polymeric cover layer 30. The piercings or cut lines 22 hence form closed, line-shaped cavities. On these cover layers 30 there are disposed ink-receiving layers 34, in particular opaque ink-receiving layers, for the further design of the polymer bank note 10 by printing technology. The ink-receiving layers 34 are disposed on the cover layers 30 over the full surface in the shown exemplary embodiment. However, it is in principle also conceivable that an ink-receiving layer is provided on the cover layer only in some regions, there being no ink-receiving layer 34 provided e.g. in the entire or in partial regions of the transmission-view region 12.

Visually, the transmission-view region 12 shows as a motif a coat of arms 24 with denomination 26, the appearance being changed in incident light and transmitted light. Additionally, the line grid formed from the cut lines 22 gives the motif region a tactile detectability, since the depressions of the cut lines 22 can be easily felt upon touching the bank notes with the fingers. The cover layers 30 protect the line grid from external influences, in particular from soiling, but retain the tactility of the motif region 12 due to their small layer thickness. The polymeric cover layers on both sides of the piercings also form a suitable continuous surface for the arrangement of further layers, in particular an ink-receiving layer. Due to the normally present elastic properties of the polymeric cover layers, it is ensured that the piercings can be felt with the fingers in particular when the depth amounts to approx. 10 µm or more and the width approx. 100 µm or more.

This tactile detectability of the motif region 12 thus constitutes, alongside the visual checkability, a further authentication feature that is easily verifiable even by a layman and cannot be imitated with a copying machine, thus offering high-quality protection from forgeries.

The visual checkability of a value document according to FIG. 2 can also be understood with reference to the optical transmittances given for the respective layers or regions. This shall be explained by a variant corresponding to FIG. 2. In the variant, a non-transparent substrate 20 has laminated thereon on both sides full-surface, transparent, polymeric cover layers 30 which are respectively provided with full-surface, opaque ink-receiving layers 34. The non-transparent substrate 20 is likewise configured over the full surface, apart from cut lines 22. The cut lines 22 constitute through-going recesses in the non-transparent substrate 20. Upon viewing of the value document in incident light, only the opaque ink-receiving layer 34 respectively lying at the front in the viewing direction is thus recognizable from both sides. The cut lines 22 of the non-transparent foil that lie therebehind are not recognizable in incident light, however. Upon viewing in transmitted light, a viewer can recognize the piercings in the opaque substrate 20, i.e. the cut lines 22, because of the non-zero transmittances of the opaque ink-receiving layers 34. Thus, a hidden security feature results. When the cut lines 22 have a smaller width than the layer thickness of the non-transparent substrate 5, as schematically represented in FIG. 2, the cut lines 22 can be perceived only in transmitted light upon substantially perpendicular viewing, which constitutes a further security feature. It will be appreciated that an object explained according to the above description also has a changed visual impression in incident light and/or transmitted light for the viewer when there is provided, instead of the non-transparent substrate 20, only an opaque substrate, i.e. a substrate with an optical transmittance greater than zero, or even only a translucent substrate, i.e. a substrate with an optical transmittance between approx. 10% and 90%. However, it must always be ensured that the optical transmittance of the substrate in the region of the piercings is greater than the optical transmittance of the substrate without piercings and greater than the optical transmittance of the ink-receiving layer.

In the exemplary embodiment of FIGS. 2 and 3, the cut lines 22 constitute complete piercings of the polymer substrate 20 which produce, besides the tactilely detectable cut-line grid, also a transmission-view region in the bank note. However, the motif region 12 can also comprise only partial piercings of the substrate, as illustrated in the exemplary embodiments of FIGS. 4 to 7. Here, there is respectively represented in the shown cross sections, for the sake of a clearer representation, only the polymer substrate 20 provided with the motif region. This situation corresponds to the state of the substrate after lasering and before the polymeric cover layers are laminated on. It will be appreciated, however, that in the finished polymer bank notes the motif region is respectively covered on both sides with a thin, polymeric cover layer and that there can here, too, be provided ink-receiving layers, protective layers or further functional layers which are respectively provided in some regions or over the full surface. In particular, there can be provided for all embodiments according to the invention an opaque ink-receiving layer with a third transmittance which is smaller than a second transmittance that is associated with the region of the piercings in the substrate. The second transmittance in the region of the piercings of the substrate is greater according to the invention than the first transmittance of the substrate outside the region of these piercings. For a value document with such an opaque ink-receiving layer, there then result interesting incident-light and/or transmitted-light effects, i.e. the visual impression of the motif region of the value document is different in incident light and/or transmitted light for a viewer, thereby clearly increasing the recognition value and thus the anti-forgery security of such a value document.

Figure 4:
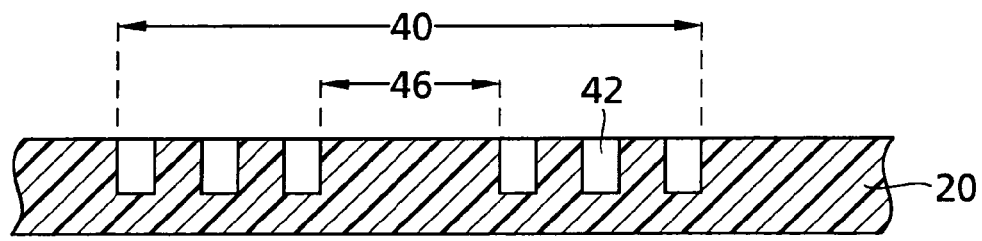

In the exemplary embodiment of FIG. 4, a line grid in the form of only partial piercings 42 of the substrate 20 has been produced by the action of laser radiation in a motif region 40 in the opaque or even non-transparent polymer substrate 20. The partial piercings form a multiplicity of thinning lines 42 in whose region the light transmission of the substrate 20 is elevated because of the smaller local layer thickness. In the case of a 50-µm-thick polymer substrate 20, the partial piercings 42 typically have a depth between 10 µm and 40 µm. In the exemplary embodiment according to FIG. 4, the preferred depth thus lies between 20% and 80% of the layer thickness of the substrate. As already mentioned hereinabove, the tactility of the motif region is influenced e.g. also by the width of the partial piercings 42.

Figure 5:
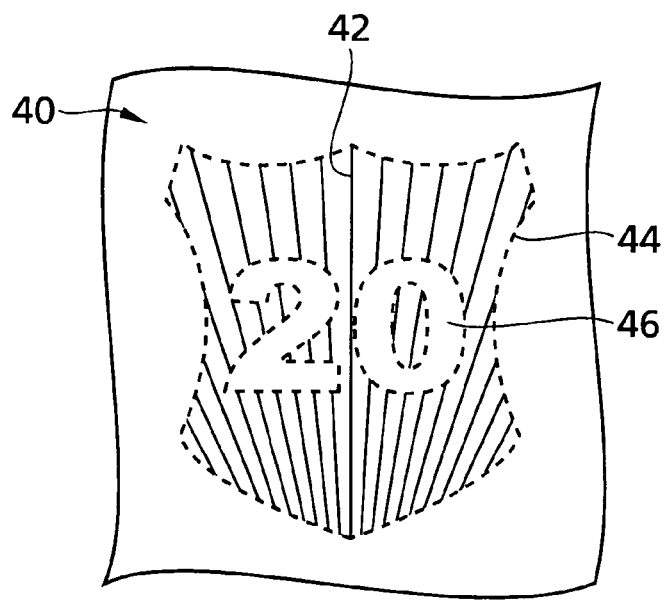

The thus produced motif region 40 shows upon viewing a watermark-like appearance wherein the represented motif is hardly recognizable in incident light, while it appears clearly in transmitted light because of the higher light transmission of the thinned regions. For illustration, FIG. 5 shows the visual appearance of the motif region 40 of an appurtenant finished polymer bank note in transmitted light. The motif region is formed in this exemplary embodiment by straight, divergent thinning lines 42 with increasing line spacing. The motif region 40 again represents with its outer outline a geometrical figure, for example a coat of arms 44 which contains in its interior a non-thinned region 46 in the form of the denomination "20" of the polymer bank note.

The motif region 40 is also tactilely detectable through the depressions in the substrate formed by the thinning lines 42 and the small layer thickness of the laminated-on cover layers. The tactility of the motif region 40 constitutes, besides the watermark-like plan-view/transmission-view effect, a further authentication feature of the polymer note that is easily checkable even by a layman.

Figure 6:
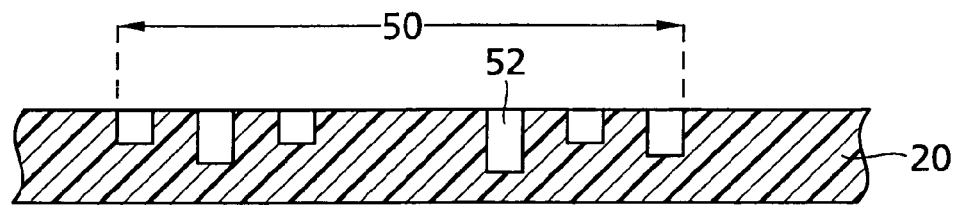

When the laser energy, more precisely, the laser irradiation, i.e. the laser energy per unit surface area, is suitably varied upon lasering, it is also possible to produce relief structures with partial piercings 52 of different depth, as shown in the exemplary embodiment of FIG. 6. While retaining the tactility of the motif region 50, there can thus be produced a multi-tone watermark-like plan-view/transmission-view effect, wherein the formed motif is practically unrecognizable upon viewing in incident light and appears with different lightness values in transmitted light because of the different degree of light transmission. Such multi-tone plan-view/transmission-view effects are particularly suitable, due to the half-tone representation thereby made possible, for relatively complex motifs, such as portrait representations.

The plan-view/transmission-view effects described with reference to the exemplary embodiment of FIG. 6 can also be explained from another vantage point by the transmittances associated with the respective regions and layers. As mentioned hereinabove, the variant of FIG. 6 has instead of complete piercings, only partial piercings 52 which reduce the layer thickness of the non-transparent substrate 20. In the region of the partial piercings 52 the layer thickness of the non-transparent substrate 20 thus varies, decreasing to zero, where applicable (see FIG. 7(a), piercings 62). Accordingly, the transmittance of the non-transparent foil 20 changes in the region of the partial piercings 52 such that the non-transparent foil is translucent or even transparent there (complete piercing 62 in FIG. 7(a)). Upon viewing in transmitted light, there thus results a pattern of transmittance over the region of the piercings 52 that is similar to that of a watermark in paper substrates. Upon viewing in incident light, the piercings 52 of the non-transparent foil 20 are hidden by the opaque ink-receiving layers. It will be appreciated that the described plan-view/transmission-view effects, also designated "incident-light/transmitted-light effects", are also perceptible to the viewer when there is provided, instead of the non-transparent substrate 20, an opaque substrate, i.e. one with a transmittance greater than zero, or even only a translucent substrate with a transmittance between approx. 10% and approx. 90%. However, it must always be ensured that the transmittance of the substrate in the region of the piercings is greater than the transmittance of the substrate without piercings and greater than the transmittance of the ink-receiving layer.

Figure 7A:
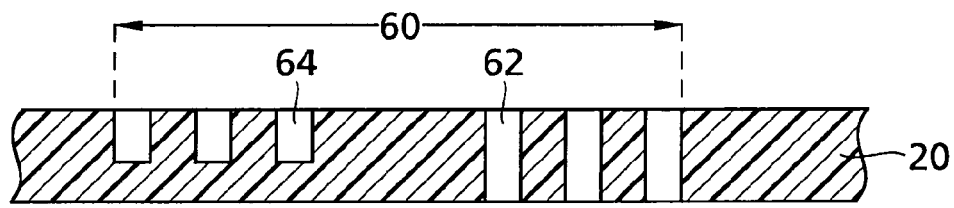
Figure 7B:
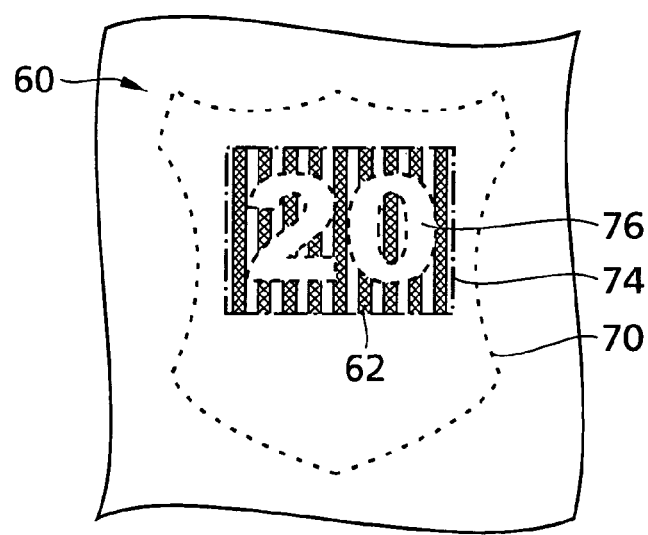
Figure 7C:
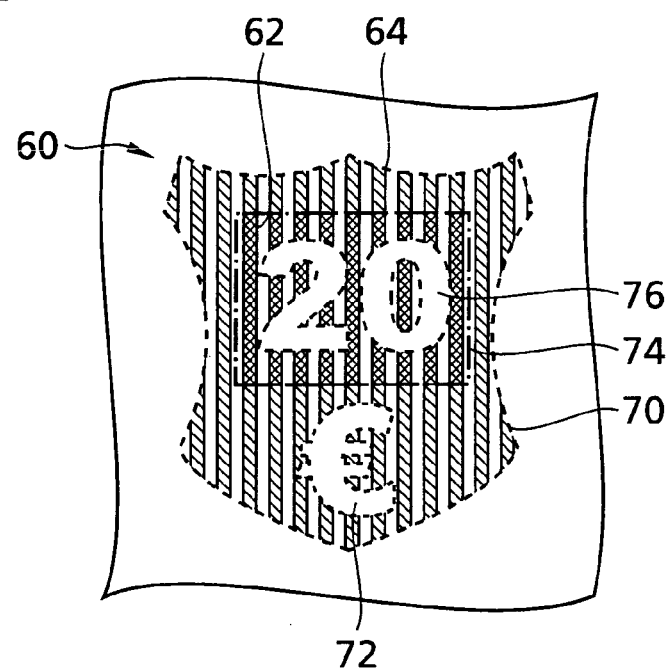

Partial and complete piercings of the polymer substrate can also be combined, as illustrated in FIG. 7. FIG. 7(a) thus shows a cross section only of the polymer substrate 20, FIG. 7(b) the visual impression of the motif region in plan view, and FIG. 7(c) the visual impression of the motif region in transmission view.

Referring first to FIG. 7(a), there has been produced in the motif region 60 by variation of the laser irradiation a tactilely detectable line grid which contains complete piercings of the substrate in the form of parallel cut lines 62, on the one hand, and only partial piercings of the substrate in the form of parallel thinning lines 64, on the other hand. The cut lines 62 and the thinning lines 64 are produced here as continuous lines in the same working operation by variation of the laser parameters, and hence adjoin each other in perfect register in the longitudinal direction.

Referring to FIG. 7(a) as well as FIG. 4 and FIG. 6, it should also be noted that, in a not specifically represented embodiment, the partial piercings in the substrate can also be made from both sides of the substrate, in mutual register, where applicable. Such a variant has extremely high anti-forgery security but simultaneously requires greater technical effort, since the partial piercings must be made from both sides of the substrate, than the embodiments shown in FIGS. 4, 6 and 7(a) wherein the partial piercings are made only from one side of the substrate.

As recognized best in the transmission view of FIG. 7(c), the thinning lines 64 form a motif region with an outer outline 70 in the form of a coat of arms. An inner region 72 not provided with thinning lines has the form of the euro symbol "€". In a rectangular cut region 74 within the motif region 60, the laser irradiation was increased upon lasering to such an extent that, instead of thinning lines, through-going cut lines 62 were produced in the substrate, which is illustrated in the figures by a narrower hatching. In the interior of the cut region 74 a non-cut region 76 was left in the form of the denomination "20" of the bank note.

When the thus produced motif region 60 is viewed in incident light, as shown in FIG. 7(b), the regions containing only the non-through-going thinning lines 64 are practically invisible, the viewer perceiving only the cut region 74 with the cut lines 62 and the uncut denomination "20" (reference sign 76). The outline and the shape of the coat of arms 70, however, are practically unrecognizable in incident light, the outline 70 being shown by a dotted line in FIG. 7(b) only to indicate its position.

When the motif region 60 is viewed in transmitted light, however, as represented in FIG. 7(c), both the regions 74 with the cut lines 62 and the regions 70 with the thinning lines 64 become visible to the viewer due to the higher light transmission. Against the bright background of the lines 62, 64, the uncut and non-thinned regions 72, 76 emerge clearly in the form of the denomination completed by the currency symbol "20€".

Since the thinning lines 64 and the cut lines 62 are produced with the same laser beam in the same working operation, they adjoin each other in perfect register in the longitudinal direction, as to be recognized in FIG. 7(c) at the upper and lower edges of the cut region 74. The cut region 74 hence fits seamlessly into the surrounding coat-of-arms motif 70 upon transmission viewing.

Such a motif completing itself in transmitted light offers a high value of attention and recognition, which is further increased by the tactile detectability of the motif region 60.

Figure 8:
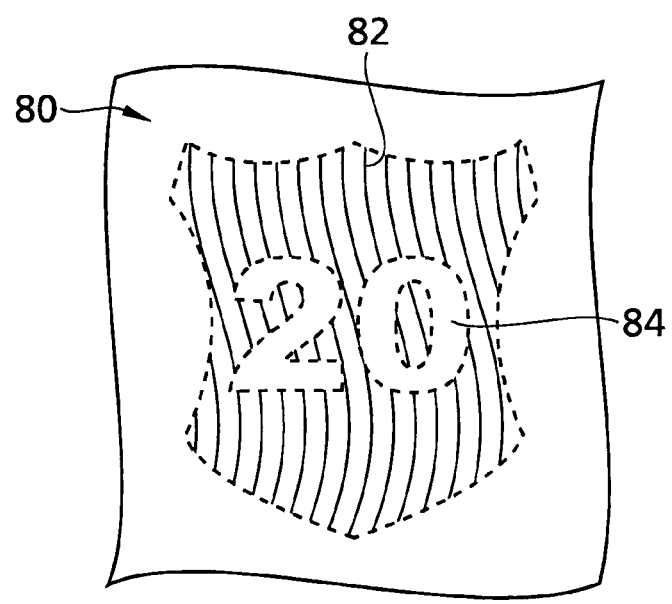

FIG. 8 shows a polymer substrate 20 with a transmission-view region 80 according to a further exemplary embodiment of the invention. As in the exemplary embodiment of FIGS. 2 and 3, the transmission-view region 80 contains a multiplicity of cut lines 82 which have been produced by lasering the opaque or even non-transparent polymer substrate 20, and which form a motif through their arrangement. As in FIG. 3, the transmission-view region 80 forms with its outer outline a coat of arms which contains in its interior an uncut region 84 in the form of the denomination "20" of the appurtenant bank note 10.

As opposed to the exemplary embodiment of FIGS. 2 and 3, however, the transmission-view region 80 is not formed by straight, but by curved, equidistant cut lines 82. Within the region 84 of the denomination, the laser power of the cutting laser was respectively lowered below the cutting threshold of the polymer substrate 20, so that no cut lines were produced there. The denomination 84 thus remains as an uncut substrate region and is clearly recognizable against the background of the gridded transmission-view region 80 primarily in transmitted light. Due to the depressions of the cut lines 82, the motif region 80 is moreover tactilely detectable, as described hereinabove.

FIG. 9 shows a further exemplary embodiment of the invention wherein the motif region 90 of a polymer substrate is formed by curved and divergent thinning lines 92. Within the region 94 of the denomination, the laser power of the cutting laser was lowered to such an extent that no thinning lines were produced there. The motif region 90 thus, like the exemplary embodiment of FIG. 5, shows a watermark-like appearance wherein the represented motif is hardly recognizable in incident light, but clearly recognizable in transmitted light. Moreover, the motif region 90 formed by the thinning lines 92 is tactilely detectable.

It will be appreciated that the shown embodiments can be combined with each other at will. For example, it is also possible to produce curved equidistant or curved divergent thinning lines of different depth. Straight and/or curved thinning lines and cut lines can also be combined with each other, as illustrated in principle in FIG. 7.

In other exemplary embodiments, there can be employed instead of the polymer substrate a substrate made of bank-note paper. The bank-note paper can consist substantially of natural fibers and/or synthetic fibers.

A value-document processing apparatus 110 in FIG. 10, which is configured in the example for processing value documents in the form of bank notes and which comprises an apparatus for checking the authenticity of value documents in the form of bank note 112, has an input pocket 114 for the input of value documents 112 to be processed, a singler 116 which can access value documents 112 in the input pocket 114, a transport device 118 with a gate 120, and, along a transport path 122 given by the transport device 118, a sensor assembly 124 disposed before the gate 120, and after the gate 120, in different branches of the transport path 122, two output pockets 126 and 128 for receiving processed value documents. A control and evaluation device 130 is connected at least to the sensor assembly 124 and the gate 120 via signal connections and serves for evaluating sensor signals of the sensor assembly 124 and actuating at least the gate 120 in dependence on the result of the evaluation of the sensor signals.

The sensor assembly 124 in connection with the control and evaluation device 130 serves for detecting properties of the value documents 112 and forming sensor signals rendering these properties. The sensor assembly 124 thus comprises at least one sensor; in this exemplary embodiment there are provided three sensors, namely, a first sensor 132, in the example an optical sensor which detects optical radiation remitted by the value document 112, a second sensor 134, in the example likewise an optical sensor which detects optical radiation transmitted through the value document, and a third sensor 136, in the example an acoustic sensor, more precisely an ultrasonic sensor which detects ultrasonic signals stemming from the value document, in particular transmitted thereby.

While a value document 112 is being transported past, the sensors 132, 134 and 136 detect, in accordance with their function, respective properties of sensing regions on the value document that are determined by the relative position of the sensors to the value document, the corresponding sensor signals thereby being formed. Each of the sensing regions has associated therewith a location that renders the position of the sensing regions for the respective sensor relative to each other and/or relative to the value document.

On the basis of the analog or digital sensor signals of the sensors 132, 134, 136, the control and evaluation device checks whether or not the value document detected by the sensors is deemed authentic and, in dependence on the result of the check, actuates the transport device 118, in particular the gate 120, such that the value document is transported in accordance with the result into one of the output pockets, for example into the output pocket 126, in the example for value documents recognized as authentic, or the output pocket 128, in the example for value documents not recognized as authentic.

The control and evaluation device 130 has for this purpose in particular, besides corresponding interfaces for the sensors, a processor 138 and a memory 140 connected to the processor 138 and storing at least one computer program with program code upon whose execution the processor 138 controls the apparatus or evaluates the sensor signals, in particular for checking the authenticity of a checked value document, and actuates the transport device 118 in accordance with the evaluation.

For this purpose, there is established by the control and evaluation device 130 upon a sensor-signal evaluation for each of the sensors at least one sensing-region property, i.e. at least one local value-document property, which is relevant for testing the value documents with regard to their authenticity. Preferably, a plurality of these properties are established. In dependence on the sensing-region properties, the control and evaluation device 130 respectively establishes for the different sensors authenticity signals that represent whether or not the established sensing properties represent an indication of the authenticity of the value document. In consequence of these signals, corresponding data can be stored in the control and evaluation device 120 for later employment.

In dependence on the authenticity signals, the control and evaluation device 130 establishes an overall result for the authenticity check according to a specified overall criterion and forms in dependence on the result a control signal for the transport device 118, in particular the gate 120. For example, the overall criterion can be such that an authenticity is only recognized when all authenticity signals represent indications of an authenticity of the value document. When this overall criterion is satisfied, the value document is thus classified as authentic, the control and evaluation device 130, by emitting the corresponding control signal, actuates the transport device 118 such that the value document is transported into the output pocket for value documents recognized as authentic, in the example the pocket 126. Otherwise, by emitting the corresponding control signal, it 130 actuates the transport device 118 such that the value document is transported into the output pocket for value documents recognized as non-authentic, in the example the pocket 128.

For processing value documents 112, value documents 112 inserted into the input pocket 114 as a stack or singly are singled by the singler 116 and fed in singled form to the transport device 118, which feeds the singled value documents 112 to the sensor assembly 124. The latter detects properties of the value documents 12, thereby forming sensor signals which render the properties of the value document. The control and evaluation device 130 detects the sensor signals, establishes in dependence thereon an authenticity rating of the respective value document, and actuates the gate 120 in dependence on the result, as described.

Figures 11, 12:
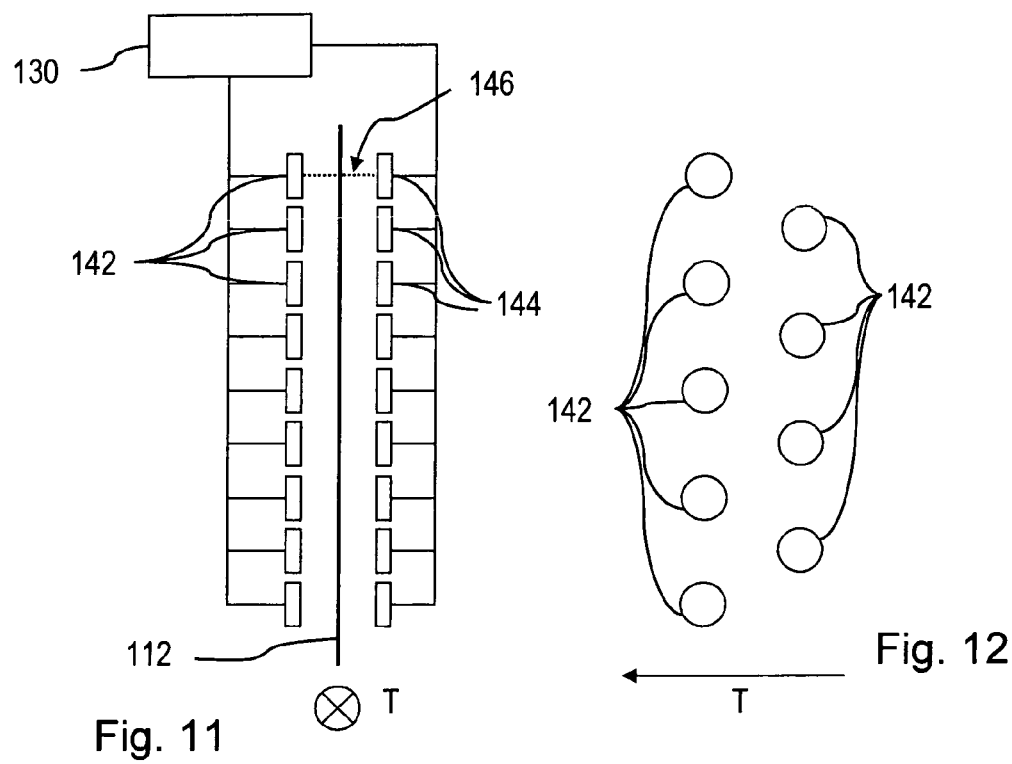

The sensor 136 is constructed in the example as follows (cf. FIGS. 11 and 12).

The sensor 136 has a plurality of ultrasonic transducers 142 disposed both transversely to a transport direction T of the value documents 112 and longitudinally thereto substantially in a plane parallel to a along the transport path 122 of the transported value documents 112, and actuated by the control and evaluation device 130, for emitting ultrasonic pulses onto the value document transported past them. These ultrasonic transducers 142 thus serve as ultrasonic transmitters.

Disposed opposite the ultrasonic transducers or transmitters 142 relative to the transport path 122 are the same number of ultrasonic transducers 144 serving as ultrasonic receivers, which so disposed to the control and evaluation device 130 via interfaces not shown in the figures and schematically shown signal connections that they can receive ultrasonic waves that emanate from a value document 112 transported along the transport path 122 and are caused by acoustic irradiation with ultrasonic pulses of the ultrasonic transmitters 142.

Each of the ultrasonic transmitters 142 has associated therewith one of the ultrasonic receivers 144 such that there results therebetween an ultrasonic path 146 extending at least approximately orthogonally to a value document 112 transported along the transport path 122, along which ultrasonic path an ultrasonic pulse emitted by the respective ultrasonic transmitter 142 runs to the ultrasonic receiver 144 associated therewith. With each pair of ultrasonic transmitters and ultrasonic receivers associated therewith or with each ultrasonic path 146 in connection with the control and evaluation device 130, it is thus possible to ascertain a value for the ultrasound transmission of the value document 112 at the acoustically irradiated location on the value document.

The ultrasonic transducers 142 or 144 are so configured that they are configured for emitting or receiving ultrasonic pulses with a duration in the range of, in the example, about 30 μs and an ultrasonic frequency, i.e. an amplitude maximum of the frequency spectrum of the ultrasonic pulse, of, in the example, about 400 kHz. Further, they are so dimensioned that a respective spot 148, i.e. sensing region, acoustically irradiated upon acoustic irradiation with the ultrasonic pulses on a value document 112 transported along the transport path 122 has a diameter of about 2 mm. Each of the sensing regions has associated therewith, as the location, the center of the sensing region.

Figure 13:
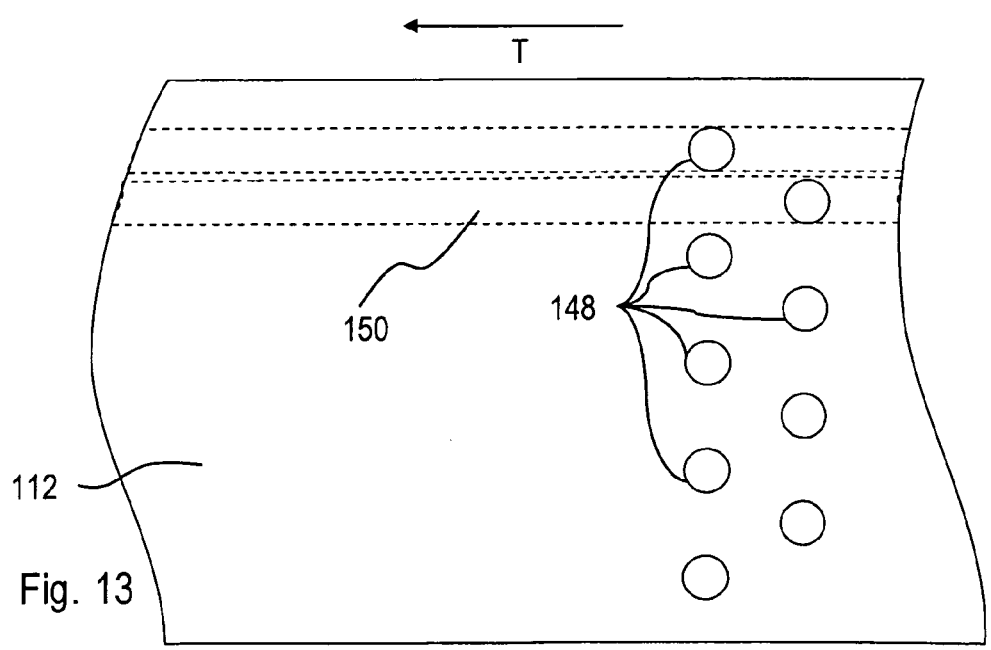

The ultrasonic transmitters 142 and ultrasonic receivers 144 are so disposed in planes parallel to the value document 112 in the transport path 122 that values for the ultrasound transmission are detectable for strip-shaped detection regions 150 extending parallel to the transport direction T, as represented in FIG. 13 for an instantaneous view during detection.

Figure 14:
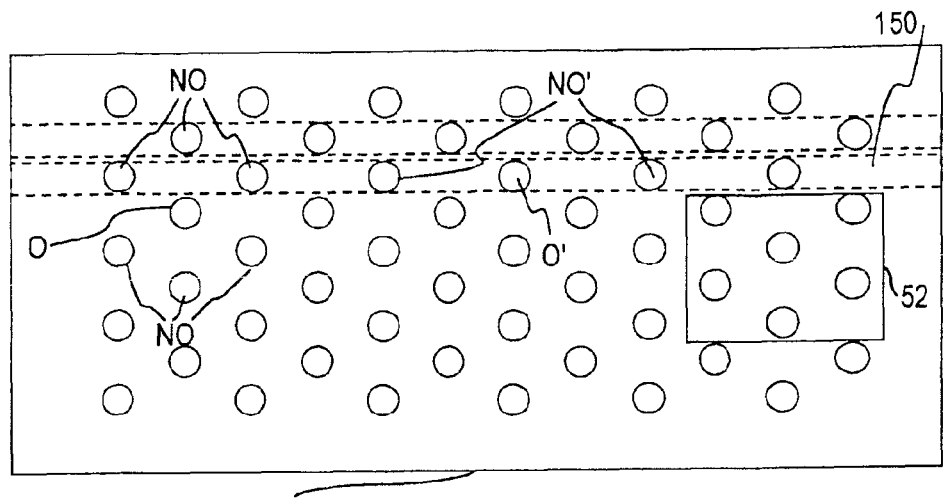

Altogether, there can thus result a distribution, represented for a value document 112 schematically in FIG. 13 and in particular FIG. 14, of sensing regions 148 or locations for which transmission values are detectable when the value document 112 is transported through the ultrasonic paths 146 at a constant, suitably specified speed and transmission values are detected at specified time intervals during said transport. In this exemplary embodiment, the actuation is effected independently of the entry of a value document 112 into the detection region of the sensor 136. To suppress an unwanted reception of ultrasonic pulse echoes, the respective ultrasonic receiver for an ultrasonic path can be switched on at a delay of somewhat less than the pulse transit time for the ultrasonic path, relative to the time when the ultrasonic pulse is emitted by the ultrasonic transmitter for the ultrasonic path, and be switched off again before twice the pulse transit time since emission.

There thus results a regular arrangement of the sensing regions or locations on the value document 112, in the example a substantially hexagonal arrangement. The arrangement of the ultrasonic transmitters 142 and ultrasonic receivers 144 is so chosen that the distance of consecutive locations in one of the strips or detection regions 150 is smaller than 1 cm. In the example, the distance of nearest neighboring locations amounts to about 1 cm.

The sensor 136 has in the exemplary embodiment in particular twenty-four ultrasonic transmitter/receiver pairs or ultrasonic paths 146, which are so disposed that the detection regions 150 or tracks have a distance between 3 and 4 mm.

For detecting the transmission values, the control and evaluation device 130 detects at constant time intervals the sensor signals of the ultrasonic receivers 144 which render the intensity or power of individual receiving ultrasonic pulses as a function of time and thus, due to the constant transport speed, also of location. Using these signals, the control and evaluation device 130 also establishes the entry of a value document into the detection region of the sensor 136. In other exemplary embodiments, such entry can also be effected in dependence on signals of other sensors and the transport speed. The transmission values are given here simply by the received ultrasonic pulse energies, assuming a basically constant transmit power of the ultrasonic transmitters 142. In other exemplary embodiments, however, it is also possible to divide the received ultrasonic pulse energies by a specified or measured ultrasonic pulse energy of transmitted pulses and thus obtain normalized transmission values.

The established transmission values are stored so as to be associated with the locations for which they were detected. This can be effected for example in such a way that the transmission values are stored in the memory 140 in the time sequence of their detection separately for each of the detection regions 150. The detection region 150 then corresponds to a coordinate in a direction transverse to the transport direction, and the position in the row along the detection region 150 to a coordinate in transport direction T.

The frequency at which the ultrasonic pulses are successively emitted and transport speed of the value document are so chosen that at least five transmission values are detected in each detection region 150 along the transport direction of the value document. In the example, transmission values are detected at a distance of 3 mm, preferably 2 mm, along the transport direction, or 60 to 90 transmission values for the detection region. However, there can also be more or fewer values.

Figure 15:
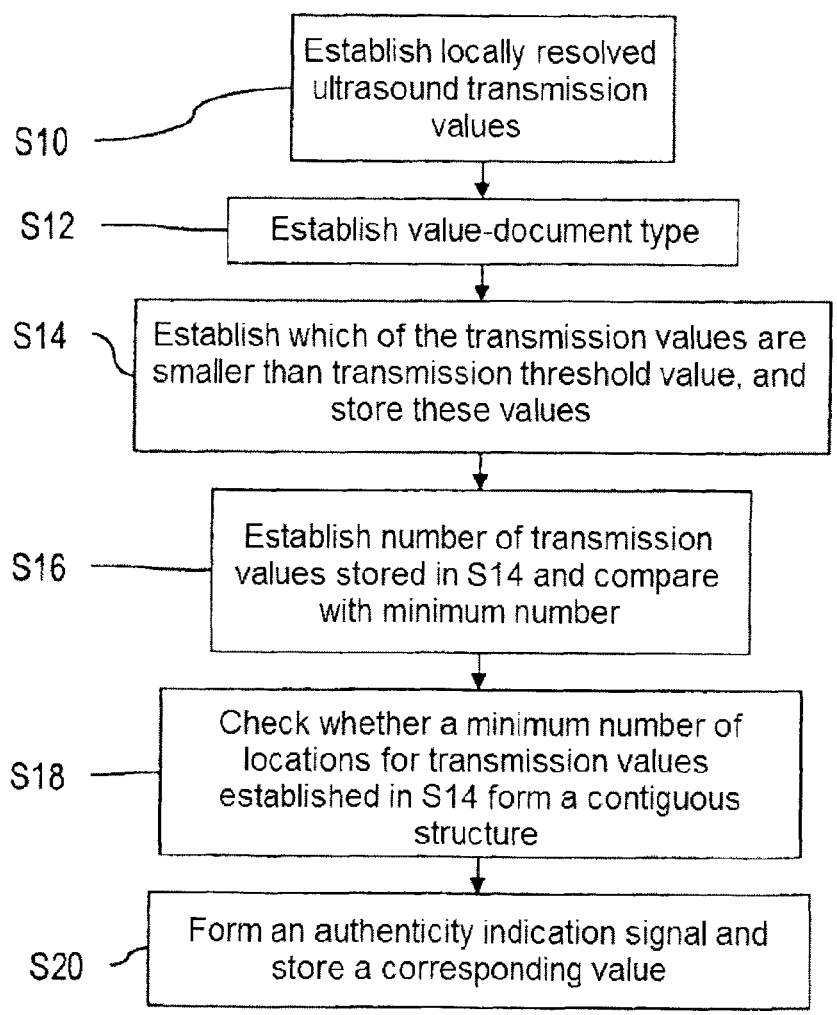
Figure 16:
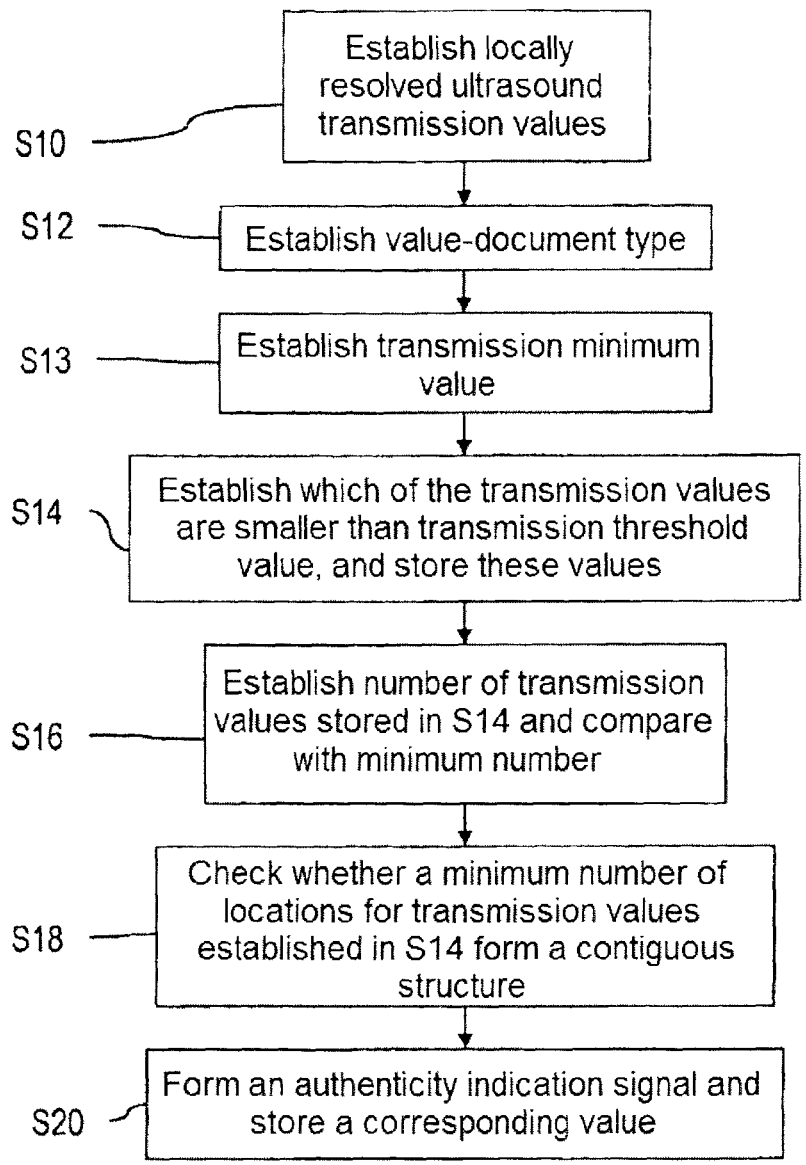
Figure 17:
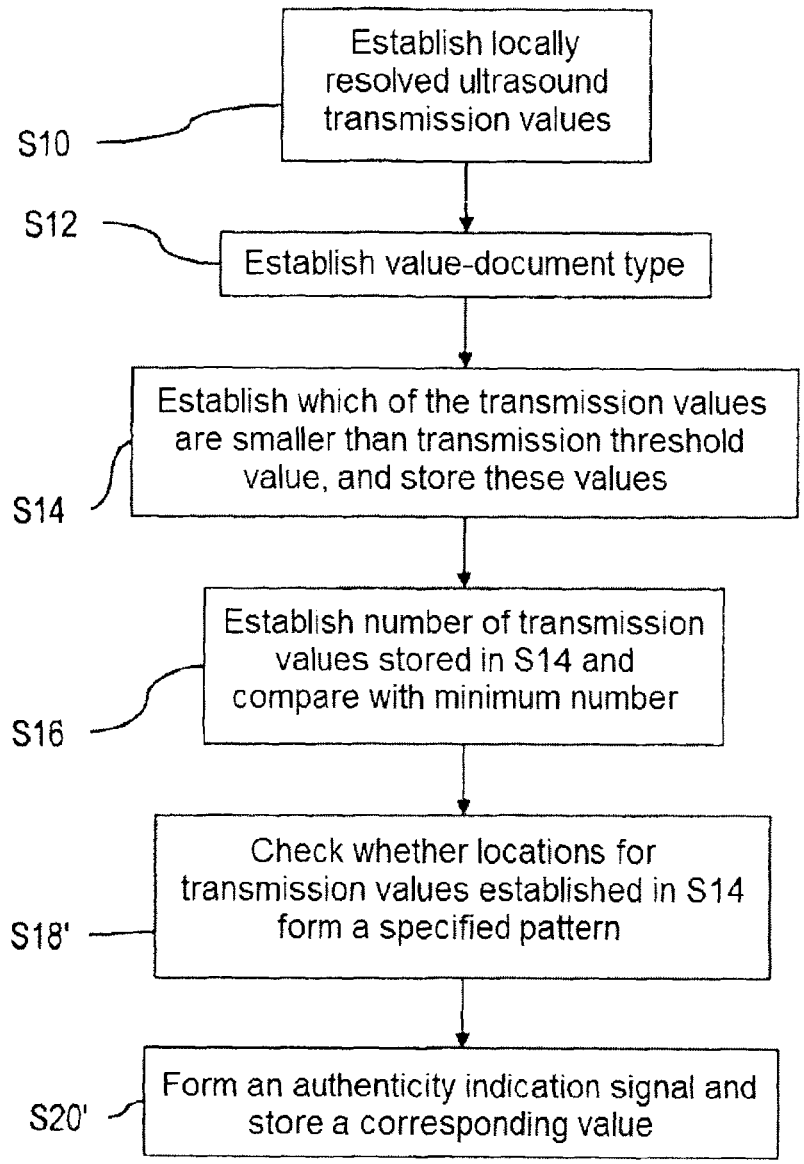

Starting out from these transmission values present for a value document as a function of location, the control and evaluation device 130, more precisely the processor 138, now carries out, when executing program code of the computer program stored in the memory 140, the following method for establishing the authenticity of the value document. The method is illustrated very schematically as a flowchart in FIG. 15.

In the described exemplary embodiment, the specified type of value document employed is the type of bank note shown in FIG. 1. In the method, there is employed a transmission threshold value which is obtained in the present example by detecting transmission values for specified reference bank notes of the stated type for a reference region without cavities, which is formed by the entire bank note except for the cavity-containing region 152, and forming an average over these transmission values. The average is multiplied by a factor between 0.1 and 0.9, in the example 0.75, the result being the transmission threshold value. The upper limit of the interval within which the transmission values must lie is set at the transmission threshold value. The lower limit is the threshold value that is employed for recognizing superimposed value-document portions or at least partly overlapping, mutually adjacent value documents of the specified type. This can be established for example by measuring the transmission values for two mutually adjacent reference value documents of the specified type, averaging the measured transmission values, and subsequently multiplying by a factor greater than 1, for example 2.

In step S10, transmission values for the transmission of ultrasound through the value document are established in a locally resolved manner by means of the ultrasonic sensor and the control and evaluation device.

In step S12, the control and evaluation device 130 establishes whether the value document has a specified value-document type and which position it has. If this is the case, the value-document type is stored for further employment. Otherwise, an error message is issued, whereupon the method is aborted. For establishing the value-document type and the position there can be employed for example the data of one of the optical sensors. Methods for this purpose are known to the person skilled in the art.

In steps S14 and S16, it is checked whether a specified number of transmission values is smaller than the specified transmission threshold value, which corresponds to a transmission that is smaller than the transmission of the reference region of the value document not having the cavity or cavities.

In step S14, the transmission values in the region specified for the value-document type, in FIG. 1 the region 152, are thus tested for whether the transmission values are smaller than the transmission threshold value specified for value documents of the specified type. This is effected in the present example by checking whether the transmission values lie within the interval specified for value documents of the specified type, or outside this interval. The region 151 is preferably chosen to be as small as possible in the example, but is so chosen that the projection of the cavities for value documents of the specified type onto the surface of the respective value document, preferably the surface of the security feature, lie within the region with certainty, i.e. taking account of the average production fluctuations during manufacture of the value documents. The surface of the security feature is understood here to be the surface of the smallest region of the surface of the value document that is formed by a closed curve and in which the projection of the cavity or the projections of the cavities lie. The locations corresponding to the transmission values lying within the interval are stored.

In step S16, it is checked whether a specified number or amount of the transmission values in the specified region 152 is greater than the transmission threshold value. The number or amount of the transmission values is specified in dependence on the type of the value document, in particular the smallest portion of the value document in which the security feature or the cavities of the security feature are disposed, and the local resolution of the ultrasonic sensor, and is to be regarded as a minimum number. For the check, the number of the transmission values lying within the interval as established in step S14 is established and compared with the minimum number. The result of the comparison is stored.

In step S18, it is additionally checked as a further criterion whether the locations corresponding to the specified number of transmission values form a contiguous structure. For this purpose, the locations corresponding to the transmission values lying within the interval are established. Thereafter it is checked whether these locations include a group with at least the minimum number which form a contiguous region, i.e. whether each one of the locations of the respective group has at least one further one of the locations of the group directly neighboring thereto.

If the checks in the steps S16 and S18 yield that the specified number was reached and the locations associated with transmission values within the interval form a contiguous region, the control and evaluation device 130 forms in step S20 a signal representing an indication of the authenticity of the security feature or of the value document.

Otherwise, the control and evaluation device 130 forms a signal representing an indication of the presence of a forgery of the value document.

The signal serves for storing a corresponding authenticity indication value.

The signal or authenticity indication value is used, as described hereinabove, with corresponding signals or authenticity indication values for the other sensors for establishing the authenticity of the value document.

A second exemplary embodiment differs from the described first exemplary embodiment in that, in a step S13 between the unchanged step S10 and a step S14' replacing the step S14, the specified transmission threshold value is established on the basis of the detected transmission values for the value document. The step S13 can be carried out before or after step S12. For this purpose, the control and evaluation device 130 establishes an arithmetic average over all transmission values detected for the value document outside the region 152. This average, lowered by 10% in the example, is employed as the specified transmission threshold value that is set as the upper limit of the interval. The lower limit remains unchanged.

A third exemplary embodiment differs from the first exemplary embodiment in that, instead of the step S18, a step S18' is performed in which, instead of checking whether the transmission values undershooting the transmission threshold value, a check is carried out that takes into consideration the distribution of those transmission values in the specified region that are smaller than the transmission threshold value. More precisely, it is checked whether the locations corresponding to transmission values that lie within the interval form the pattern comprising the region 24 with cavities and, configured therein, the region 26 without cavities as recognizable in FIG. 3.

If the checks in the steps S16 and S18' yield that the specified number was reached and the locations associated with transmission values within the interval have the specified distribution, i.e. form the specified pattern here, the control and evaluation device 130 forms, in a step S20' replacing the step S20, a signal representing an indication of the authenticity of the security feature or of the value document.

The further processing is effected as in the first exemplary embodiment.

A further exemplary embodiment differs from the first exemplary embodiment in that the step S18 is omitted, and in a step S20" corresponding to the step S20 the signal is formed only in dependence on the result in step S16.

Yet other exemplary embodiments differ from the above-described exemplary embodiments in that not only transmission values in the region 152 are checked, but all transmission values. Groups of transmission values are then sought that are given by the locations associated with the transmission values forming a contiguous structure. Among these, groups are then sought whose number of transmission values is greater than the minimum number. Finally, the position of the locations corresponding to the transmission values of the group is then established on the value document.

When a group is found and its locations lie within the specified region 152, a signal is formed or a value is stored which signal or value represents an indication of the authenticity of the value document.

Further exemplary embodiments differ from the above-described exemplary embodiments in that the ultrasonic transmitters and ultrasonic receivers are so disposed that the ultrasonic paths respectively formed therebetween extend so as to be inclined relative to the transport plane in which value documents are transported through the ultrasonic sensor. In this case, ultrasound can also be emitted as continuous sound, with the receivers being modified accordingly.

Yet other exemplary embodiments differ from the above-described exemplary embodiments in that there is employed instead of a polymer substrate a substrate made of bank-note paper in which the cavity-forming piercings are configured. The bank-note paper can consist substantially of natural fibers and/or synthetic fibers.

The invention claimed is:

1. A method for examining a sheet-shaped or card-shaped value document of a specified type with a security feature having one or more cavities configured in the value document, the width of the cavity or cavities in at least one respectively specified direction exceeding 10 μm, the method comprising the steps of:

establishing, in a locally resolved manner, transmission values for the transmission of ultrasound in a specified frequency range, checking whether a specified number of the transmission values is smaller than a specified transmission threshold value which corresponds to a transmission that is smaller than the transmission of at least one reference region of the value document or of at least one reference value document not having the cavity or cavities, and in dependence on the result of the checking step, forming a signal which represents an indication of the authenticity of the value document and/or which represents an indication of the presence of a forgery of the value document.

2. The method according to claim 1, wherein the ultrasound has a frequency in the range of 50 kHz to 800 kHz.

3. The method according to claim 1, wherein ultrasonic pulses are employed for establishing the transmission values.

4. The method according to claim 1, wherein the transmission threshold value is determined using the established transmission values.

5. The method according to claim 1, wherein the transmission threshold value was established by examinations of reference value documents of the same type.

6. The method according to claim 1, wherein upon the check it is established whether the respective transmission value lies within a specified interval whose upper limit is the transmission threshold value.

7. The method according to claim 1, wherein only transmission values for a specified region of the value document are used when performing the checking step.

8. The method according to claim 7, wherein the checking step further includes checking whether the distribution of the transmission values in the specified region and/or of those transmission values in the specified region that are smaller than the transmission threshold value satisfies a specified distribution criterion.

9. The method according to claim 1, wherein it is additionally checked whether the locations corresponding to the specified number of transmission values forms a contiguous structure.

10. The method according to claim 1, wherein an extension of the cavity or cavities in the or another direction specified for the respective cavity, parallel to a surface of the value document, is greater than 100 μm.

11. The method according to claim 1, wherein an extension of the cavity or cavities in a direction perpendicular to a surface of the value document is greater than 30% of the total thickness of the value document in the region of the cavity or cavities and/or greater than 20 μm.

12. The method according to claim 1, wherein the cavity or at least two of the cavities are of line-shaped configuration.

13. The method according to claim 1, wherein the value document comprises a substrate which has partial or complete piercings, and the piercings are covered on both sides by cover layers held on the substrate, and the covered piercings form the cavities.

14. The method according to claim 13, wherein the piercings are disposed in a motif region of the value document.

15. The method according to claim 14, wherein the motif region has a changed visual impression in incident light and/or transmitted light, and/or is configured in the form of a pattern, signs or an encoding.

16. The method according to claim 13, wherein the piercings are of line-shaped configuration and have a width between 0.05 mm and 1 mm.

17. An apparatus for examining a value document with a security feature having one or more cavities configured in the value document, the width of the cavity or cavities in at least one respectively specified direction exceeding 10 μm, the apparatus comprising:
- an ultrasound transmission sensor for detecting locally resolved transmission values for the transmission of ultrasound in a specified frequency range through the value document;
- a control and evaluation device connected to the ultrasound transmission sensor via a signal connection for evaluation thereof;
- a transport device for transporting the value document through the ultrasound transmission sensor, wherein the transmission values are detected during the transport of the value document through the ultrasound transmission sensor;
- wherein the control and evaluation device is configured for checking whether a specified number of transmission values is smaller than a specified transmission threshold value corresponding to a transmission smaller than the transmission of at least one reference region of the value document or of at least one reference value document not having the cavity or cavities, and
- for forming a signal which represents an indication of the authenticity of the value document and/or which represents an indication of the presence of a forgery of the value document in dependence on the result of the checking step.

18. The apparatus of claim 17, further comprising a data processing device which has a field-programmable gate array (FPGA).

19. The apparatus of claim 17, further comprising a data processing device which has a microcontroller.

20. The apparatus of claim 17, further comprising a data processing device which has a processor and a memory with a data processing program stored therein.

* * * * *